United States Patent
Bailey, III et al.

(10) Patent No.: US 7,429,671 B2
(45) Date of Patent: Sep. 30, 2008

(54) PROCESS FOR THE FLUORINATION OF BORON HYDRIDES

(75) Inventors: Wade H. Bailey, III, Emmuas, PA (US); William Jack Casteel, Jr., Emmaus, PA (US); Sergei Vladimirovich Ivanov, Schnecksville, PA (US); Xukun Luo, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 124 days.

(21) Appl. No.: 11/634,735

(22) Filed: Dec. 6, 2006

(65) Prior Publication Data

US 2008/0138269 A1    Jun. 12, 2008

(51) Int. Cl.
C07F 5/02 (2006.01)
C07F 9/02 (2006.01)

(52) U.S. Cl. ............... 556/7; 556/8; 568/3; 568/4; 568/6

(58) Field of Classification Search .............. 556/7, 556/8; 568/3, 4, 6
See application file for complete search history.

(56) References Cited

U.S. PATENT DOCUMENTS

| | | | |
|---|---|---|---|
| 3,551,120 | A | 12/1970 | Miller et al. |
| 6,130,357 | A | 10/2000 | Strauss et al. |
| 6,180,829 | B1 | 1/2001 | Strauss et al. |
| 6,335,466 | B1 | 1/2002 | Strauss et al. |
| 6,781,005 | B1 | 8/2004 | Casteel, Jr. et al. |
| 2005/0053841 | A1 | 3/2005 | Ivanov et al. |

OTHER PUBLICATIONS

U.S. Appl. No. 10/655,476, filed Sep. 4, 2003, Ivanov, Sergei et al.
U.S. Appl. No. 10/924,293, filed Aug. 23, 2004, Ivanov, Sergei et al.
U.S. Appl. No. 11/197,478, filed Aug. 5, 2005, Ivanov, Sergei et al.
U.S. Appl. No. 11/372,907, filed Mar. 10, 2006, Ivanov, Sergei et al.
Canterford, J. H. et al; "Manipulation of Volatile Fluorides and Other Corrosive Compounds;" Interscience Pubs., New York. H. Jonassen and A. Weissberger eds., 1968; pp. 273-306.
O'Donnell, T "Superacids and Acidic Melts as Inorganic Chemical Reaction Media"; Chapter 3: Lewis Acidity in Protonic Superacids, VCH Publishers, NY;1993. pp. 55-80.
Knoth, W.H. et al: "Chemistry of Boranes; IX. Halogenation of $B_{10}H_{10}^{-2}$ and $B_{12}H_{12}^{-2}$;" Inorganic Chemistry; (1964) pp. 159-167.
N. Kusnetsov and N. Zhukova, et al. *Zh. Neorg. Khim.* "Synthesis and Physicochemical Properties of Potassium Difluorodecahydro-closo-dodecaborate." 25, 3 (1980) 690-694.
N. Kuznetsov and N. Zhukova et al. *Zh. Neorg. Khim.* "Synthesis and Physicochemical Properties of New Fluoro-Substituted -closo-dodecaborates." 25, 11 (1980) 2939-2942.
N. Kuznetsov and K. Solntsev, et al. "The Polyhedral $B_{12}H_{12}^{2-}$ Anion as a Three-Dimensional Aromatic System;" Plenum Publishing Corporation (1992) USD 546,271; (1992) pp. 296-317.
S. Ivanov and K. Solntsev, et al. "Stereochemical Aspects of the Fluorination of the $B_{12}H_{12}^{2-}$ Anion." *Koord. Khim*; 23, 6 (1997) 370-376.
S. Ivanov and S. Strauss, et al;. "Fluorination of Deltahedral Closo-Borane and —Carborane Anions with N-Fluoro Reagents." *F. Fluorine. Chem.* 89 (1998) pp. 65-72.
S. Ivanov and S. Strauss, et al. "Synthesis and Characterization of the Anionic Fluorocarboranes $6,7,8,9,10\text{-}Cb_9H_5F_5^-$, $6,7,8,9\text{-}CB_9H_5F_4\text{-}10\text{-}OH^-$, and $6,7,8,9\text{-}CB_9H_5F_4\text{-}10\text{-}CHCOCH_3$." *Inorg. Chim. Acta.* 289 (1999) 76-84.
S. Ivanov and S. Strauss, et al. "Fluorination of $B_{10}H_{10}^{2-}$ with an N-Fluoro Reagent. A New Way To Transform B-H into B-F Bonds." *Inorg. Chem.* 35, 24 (1996) pp. 6914-6915.
W. Baker and A. Mossman. *Matheson Gas Data Book*. Matheson Gas Products, Secaucus, NJ, 1980. pp. 391.
A. Balagurova and V. Lebedev, et al. . "Selective Fluorination of *o*- and *m*-carboranes. Synthesis of 9-monofluor-, 9,12-difluoro, 8,9,12-trifluoro-, and 8,9,10,12-tetrafluoro-*o*-carboranes and 9-monofluoro, and 9,10-difluoro-*m*-carboranes. Molecular Structure of 8,9,10,12-tetrafluoro-*o*-carborane." *J. Organometallic. Chem*; 385 (1990) pp. 307-318.

*Primary Examiner*—Yvonne Eyler
*Assistant Examiner*—Jennifer Y Cho
(74) *Attorney, Agent, or Firm*—Michael K. Boyer

(57) ABSTRACT

A process for fluorination of borohydride salts including providing a reaction medium comprising HF and a superacid. A borohydride salt compound is added to the reaction medium. The borohydride salt is reacted with the reaction medium under conditions to form a fluorinated borohydride salt. In addition, reactor vessels may be provided for reacting the HF, superacid additive and borohydride that are fabricated from materials resistant to superacid compositions.

18 Claims, No Drawings

PROCESS FOR THE FLUORINATION OF BORON HYDRIDES

CROSS-REFERENCE TO RELATED APPLICATIONS

The subject matter of this invention is related to U.S. patent application Nos. Ser. 10/655476, filed on Sep. 4, 2003 issued as U.S. Pat. No. 7,311,993 on Dec. 25, 2007 ; Ser. No. 10/924293, filed on Aug. 23, 2004 issued as U.S. Pat. No. 7,348,103 on Mar. 25, 2008 ; Ser. No. 11/372907, filed on Mar. 10, 2006, and Ser. No. 11/197478, filed on Aug. 5, 2005. The disclosure of the previously identified patent applications is hereby incorporated by reference.

The present invention is directed to methods for fluorinating boron hydride compounds.

BACKGROUND OF THE INVENTION

Fluorinated boron hydride anions are weakly coordinating anions and have been used as electrolytes and as catalytic components, particularly to enhance the catalytic activity of metal cations finding use in a variety of reactions.

The substitution of borohydrides, including polyhedral closo-boranes and closo-carboranes with fluorine to various degrees has previously been afforded by employing a number of methods. For example, the direct fluorination of these exemplary boron hydrides with elemental fluorine ($F_2$) have been reported and readily provides highly fluorinated and mixtures of partially fluorinated products. N—F fluorinating agents have also been employed in obtaining mixtures of partially fluorinated products. N—F fluorinating agents suffer from the drawback that they are often accompanied by difficulties associated with impurities formed by the participation and undesirable substitution of the solvent. The fluorination methods listed above, while capable of providing partially fluorinated products, all suffer from the drawback that they typically produce mixtures of products with various isomers and relatively wide ranges of degrees of fluorination.

HF has also been utilized to fluorinate borohydrides. Reactions of $B_{12}H_{12}^{2-}$ salts and monocarboranes with HF typically provide an advantage in giving rise to products with narrow ranges for degrees of fluorination. The degree of fluorination is progressive through selective, well-established stereochemistry and may be controlled primarily by varying the reaction temperature such that $B_{12}H_{12}^{2-}$ is reported to provide the substitution of only six fluorine atoms at 150-210° C. and monocarboranes are reported to provide the substitution of only 3-4 fluorine atoms in the same temperature range. Additional fluorine atoms can be substituted but under considerably more forcing conditions. These conditions are undesirable for industrial processes because the critical temperature for HF is 188° C. Such high temperature HF is damaging to equipment and dangerous to handle.

Another method for fluorination of boron compounds includes U.S. Pat. No. 3,551,120, which discloses boron compounds of the formula $M_a(B_{12}H_{12-y}X_y)_b$ where M is a cation having a valence of 1-4, and $(B_{12}H_{12-y}X_y)$ is a group which forms a divalent anion in an aqueous solution. The term M represents hydrogen, ammonium, and metal cations, e.g., groups I, II VIII, IIIb and so forth. X represents halogen, (F, Cl, Br, and I), carboxyl, nitro, nitroso, sulfonyl, and so forth. Example 1 shows the formation of $Cs_2B_{12}H_7F_5$ by effecting fluorination of $CsB_{12}H_{11}OH$ in anhydrous HF. The temperatures utilized by this process are undesirably high in that the temperatures are above the critical temperature for HF.

U.S. Pat. No. 6,180,829 discloses metal compounds of polyhalogenated heteroborane anions of the formula $M[R_aZB_bH_cF_dX_e(OR'')_f]_k$ where M is a cation having a valence of from 1-4, e.g., an alkali or alkaline earth metal cation, R typically is a halogen or an alkyl group, Z is C, Si, Ge, Sn, Pb, N, P, As, Sb, and Bi; X is a halide and R'' is a polymer, hydrogen, alkyl and the like. The subscripts represents integers. Example 2 shows the formation of the polyfluorinated monocarborane anion from a monocarborane hydride wherein $CsCB_{11}H_{12}$ is reacted with a mixture of HF and 10% $F_2$ in N2. CsCB11F11H was recovered as a white solid. Significant cluster decomposition occurred during the fluorination, and yields were 50-60% at these loadings. U.S. Pat. No. 6,448,447, a continuation-in-part of U.S. Pat. No. 6,180,829 and others, discloses in Example 11 the formation of $K_2B_{12}F_{12}$ (1 g) by the continuous addition of a fluorine/nitrogen gas phase to a suspension of $K_2B_{12}H_{12}$ in HF. This process suffers from the drawback that the distribution of fluorinated products is undersirably broad. In addition, the process utilizes expensive reagents, such as $F_2$.

Knoth et al, Chemistry of Boranes, IX. Fluorination of $B_{10}H_{10}^{-2}$ and $B_{12}H_{12}^{-2}$ Inorganic Chemistry, Vol. 2, No. 2, February 1964 disclose the preparation of highly fluorinated dodecaborates, by (a) effecting fluorination with anhydrous HF alone to a composition up to $B_{12}F_6H_6^{2-}$, and (b) effecting the direct fluorination of a 5 wt. % $B_{12}H_{12}^{2-}$ potassium salt by contacting the salt with $F_2$ in the presence of water (under these conditions, the HF concentration is never >10% and thus the Hammett acidity, $H_o$ remains >0 throughout the fluorination). The reaction when conducted in the presence of water was difficult to run to completion as evidenced by the use of a 5-fold excess of fluorine. In the end, a low yield (32%) of a hydroxy substituted fluoroborate, $B_{12}F_{11}(OH)^{2-}$, was obtained rather than the desired fluorine substituted dodecaborate.

Solntsev, et al, Stereochemical Aspects of the Fluorination of the $B_{12}H_{12}^{-2}$ Anion, Russian Journal of Coordination of Chemistry, Vol. 23, No. 6, 1997, pp 369-376, disclose that the reaction of supercritical HF with $K_2B_{12}H_{12}$ at 600° C. generates the fully fluorinated anion. Significant decomposition was observed and yields of only 25% were obtained under these conditions.

A stoichiometric oxidative fluorinating agent, antimony pentafluoride ($SbF_5$), has been employed in the fluorination of borohydrides, including o- and m-carboranes. The $SbF_5$ utilized in the fluorination of borohydrides previously known acts as a stoichiometric oxidative fluorinating agent, wherein this role of $SbF_5$ is well documented. The use of superacids, apart from HF alone, in aiding the fluorination of borohydrides is not known in the art.

Thus, what is needed is a process that provides selective and controlled fluorination of borohydrides with facile, high-yielding synthesis of fluorinated boron compounds of narrow and controlled degrees of fluorination under reaction conditions that are industrially practicable. The present invention provides these advantages as well as other related advantages.

The disclosure of the previously identified U.S. Patents is hereby incorporated by reference.

BRIEF SUMMARY OF THE INVENTION

The present invention provides a method for reacting at least one borohydride salt with anhydrous hydrogen fluoride (HF) and at least one superacid additive to affect the conversion of B—H bonded centers to B—F bonded centers in a controlled and selective manner by varying reaction conditions such as temperature, concentration, superacid additive composition, observance of well-established superacidic HF norms, and reactor materials of construction. Super Acid "SA" is defined as a compound or mixture of compounds capable of having an acidity or activity (e.g., enhancing the ability to add F to the borohydride precursor) in anhydrous HF that is equal to or greater than substantially pure HF. This invention is efficient when relatively non-oxidizing superacid additive, such as boron trifluoride ($BF_3$), tantalum pentafluoride ($TaF_5$), among others, are employed. If desired, the superacid additive can be mixed with another acid that is capable of forming an SA, or the HF can be combined with at least one other acid and combined with superacid additive.

One aspect of the invention includes a process for fluorination of borohydride salts including providing a reaction medium comprising HF and at least one superacid additive. A borohydride salt compound is added to the reaction medium. The borohydride salt has the following formula:

$$M_a[R_bZ_cB_dH_eF_y]_k$$

wherein M is a cation having a valence from 1-4; R is selected from the group consisting of a halogen group, hydroxyl group, amino group, nitro group, alkyl group, alkoxy group, perfluoroalkoxy group, phenyl group and combinations thereof; Z is selected from the group consisting of C, Si, Ge, Sn, Pb, N, P, As, Sb, Bi and combinations thereof; B is boron; H is hydrogen; F is fluorine; a is 1 or 2; b is an integer from 0 to 11, c is 0 or 1; d is an integer from 5 to 12; e is an integer from 1 to 12; and y is an integer from 0 to 11; k is 1, 2, or 3. The borohydride salt is reacted with the reaction medium under conditions for formation of a fluorinated borohydride salt having the formula:

$$M_a[R_bZ_cB_dH_{e-n}F_{y+n}]_k$$

wherein n is an integer from 1 to e. The fluorinated borohydride formed may also include a degree of fluorination (i.e., [y+n]) of equal to or greater than 5.

Another aspect of the invention comprises a process for fluorination of borohydride salts including fluorinating a borohydride salt compound in the presence of a superacid and HF in a reactor vessel fabricated from a material resistant to superacid compositions to form a compound having the following formula:

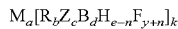
$$M_a[R_bZ_cB_dH_{e-n}F_{y+n}]_k$$

wherein M is a cation having a valence from 1-4; R is selected from the group consisting of a halogen group, hydroxyl group, amino group, nitro group, alkyl group, alkoxy group, perfluoroalkoxy group, phenyl group and combinations thereof; Z is selected from the group consisting of C, Si, Ge, Sn, Pb, N, P, As, Sb, Bi and combinations thereof; B is boron; H is hydrogen; F is fluorine; a is 1 or 2; b is an integer from 0 to 11, c is 0 or 1; d is an integer from 5 to 12; e is an integer from 1 to 12; and y is an integer from 0 to 11; k is 1, 2, or 3; and n is an integer from 1 to e. The fluorinated borohydride formed may also include a degree of fluorination (i.e., [y+n]) of equal to or greater than 5.

Still another aspect of the invention includes a fluorinated borohydride containing composition comprising hydrogen, at least one superacid additive and a compound having the following formula:

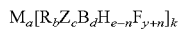
$$M_a[R_bZ_cB_dH_{e-n}F_{y+n}]_k$$

wherein M is a cation having a valence from 1-4; R is selected from the group consisting of a halogen group, hydroxyl group, amino group, nitro group, alkyl group, alkoxy group, perfluoroalkoxy group, phenyl group and combinations thereof; Z is selected from the group consisting of C, Si, Ge, Sn, Pb, N, P, As, Sb, Bi and combinations thereof; B is boron; H is hydrogen; F is fluorine; a is 1 or 2; b is an integer from 0 to 11, c is an integer from 0 to 1; d is an integer from 5 to 12; e is an integer from 1 to 12; and y is an integer from 0 to 11; k is 1, 2, or 3; and n is an integer from 1 to e. The fluorinated borohydride may also include a degree of fluorination (i.e., [y+n]) of equal to or greater than 5.

Another aspect of the present invention relates to a composition obtained by combining the aforementioned borohydride formulations and at least one super acid.

An advantage of the present invention includes selective and controlled fluorination of borohydrides with facile, high-yielding synthesis of fluorinated boron compounds of narrow and controlled degrees of fluorination under reaction conditions that are industrially practicable.

Another advantage of the present invention includes an ability to achieve high levels of fluorination of the borohydride anions.

Still another advantage of the present invention includes an ability to achieve higher yields and reaction efficiency.

Still another advantage of the present invention includes an ability to achieve high loadings of reactant in the carrier, and an ability to minimize yield loss due to byproduct formation.

Other features and advantages of the present invention will be apparent from the following more detailed description of certain aspects or embodiments, taken in conjunction with the accompanying drawings which illustrate, by way of example, the principles of the invention.

DETAILED DESCRIPTION OF THE INVENTION

This invention relates to a process for the fluorination of borohydride salts, including the exemplary salts of $B_{12}H_{12}^{-2}$ and $CB_{11}H_{12}^{-1}$, comprising the formula $M_a[R_bZ_cB_dH_eF_y]_k$ (I). The process may comprise fluorination by contact with a minimum quantity n molar equivalents of HF and at least one superacid additive (denoted herein as "SA") to produce product compounds of the formula $M_a[R_bZ_cB_dH_{e-n}F_{y+n}]_k$ (II) and is summarized by the equation:

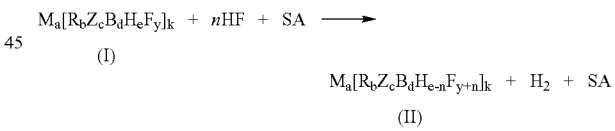

$$M_a[R_bZ_cB_dH_eF_y]_k + n\text{HF} + \text{SA} \longrightarrow$$
$$(\text{I})$$
$$M_a[R_bZ_cB_dH_{e-n}F_{y+n}]_k + H_2 + \text{SA}$$
$$(\text{II})$$

where M is a cation having a valence from 1-4, e.g., a proton, alkali metal, or alkaline earth metal cation; R may include halogen, hydroxyl, amino, nitro, alkyl group, alkoxy group, perfluoroalkoxy group, or phenyl group; Z is C, Si, Ge, Sn, Pb, N, P, As, Sb, or Bi; B is boron; H is hydrogen; F is fluorine; a is 1 or 2; b is an integer from 0 to 11, c is an integer from 0 to 1; d is an integer from 5 to 12; e is an integer from 1 to 12; y is an integer from 0 to 11; k is 1, 2, or 3, the respective values of a and k being determined by the valence of M, that is, when the integer a is multiplied by the valence of M it is equal to the integer k or 2 times the integer; and n is an integer from 1 to e wherein said borohydride salt compound I is contacted with HF and a superacid under conditions for formation of the said fluorinated product compound II. For example, salts of dodecahydrododecaborate ($B_{12}H_{12}^{2-}$) can be treated with superacidic HF thereby affecting consecutive fluorinations to provide salts of $B_{12}F_xH_{12-x}^{2-}$ where x can be from 3 to 10 and can have a distribution range of 1-3 fluorines. The method of the present invention is particularly suitable for preparing fluorinated compounds having higher degrees of fluorination with a narrow distribution of fluorinated products. Specifically, the fluorinated product compound II can include a degree of fluorination (i.e., [y+n]) of equal to or greater than 5, including degrees of fluorination greater than or equal to 6 and degrees of fluorination greater than or equal to 8.

For both salt compounds I and II, M comprises a cation that may be selected based on its desired interaction with the corresponding $[R_bZ_cB_dH_{e-n}F_{y+n}]$ anion, HF, or the superacid additive to affect acidity, solubility, reaction rate, ease of isolation, degree of fluorination, or other reaction system properties. Examples of M cations comprise at least one member from the group consisting of hydrogen, hydronium ($H_3O^+$), ammonium, tetraalkylammonium, trialkylammonium, alkali metals, alkaline earth metals, tetraalkylphosphonium, and transition metals such as zinc, silver, iron, nickel, tantalum, and cerium. Desirable results have been obtained cations are represented by hydrogen, the alkali metals, and alkaline earth metals.

The borohydride precursor compound I as described above can be represented by numerous compositions. The $[R_bZ_cB_dH_eF_y]$ anion is represented as a polyhedral, boron-containing cluster bearing B—H bonds. The backbone of the cluster, Z and B as broadly defined above and represented by simple examples, such as $B_{12}H_{12}^{2-}$ and $CB_{11}H_{12}^-$, is generally a polyhedral core structure bearing the pendant groups R, H, and F, which may be positioned by design to affect the subsequent desired substitution pattern of F for H.

The ability to fluorinate different forms of compound I may vary greatly depending the actual constitution of the $[R_bZ_cB_dH_eF_y]$ anion. Thus, the composition of compound I may vary since the invention broadly permits the more facile conversion of B—H bonds to B—F bonds through the use of superacidic HF as demonstrated in the Examples by fluorination of $B_{12}H_{12}^{2-}$.

HF is provided as a reactant to affect the fluorination of precursor compound I. HF may be present in amounts ranging from a stoichiometric or limiting reagent to very dilute liquid systems where HF comprises about 99% or greater by weight the total mass of reactants. The amount of HF is typically about 60% to about 95% by weight of the total mass of all reactants to act as a solvent and liquid transfer medium where the greater concentrations of HF are useful to achieve the highest degrees of fluorination. HF may also be used in the presence of a second liquid as a solvent or transfer medium; examples of such alternate liquids comprise but are not limited to $SO_2ClF$, $SO_2$, perfluorinated liquids such as KRYTOX® and FOMBLIN® fluids, chlorofluorocarbons, hydrochlorofluorocarbons and hydrofluorocarbons. KRYTOX® is a federally registered trademark of E. I. DU PONT DE NEMOURS AND COMPANY CORPORATION, Wilmington, Del. for perfluorinated liquids. FOMBLIN® is a federally registered trademark of AUSIMONT S.P.A. COMPANY, Milan, Italy for perfluorinated liquids.

The superacid (SA) may be selected in order to enhance the acidity of the reaction system by complexing basic fluorides, by complexing or reacting with adventitious moisture or other basic materials such as alcohols and amines, and/or by tuning the acidity in a manner believed to affect the equilibrium of increasing or maximizing the concentration of M associated with the anion $[R_bZ_cB_dH_eF_y]$, its intermediates and products as a proton. SA is defined as a compound or mixture of compounds capable of having an acidity or activity (e.g., enhancing the ability to add F to the borohydride precursor) in anhydrous HF that is equal to or greater than substantially pure HF.

Examples of suitable compositions for the SA comprise but are not limited to Lewis acids such as $AlCl_3$, $AlF_3$, $BCl_3$, $BF_3$, $GaF_3$, $VF_5$, $NbF_5$, $TaF_5$, $PCl_5$, $PF_5$, $AsF_5$, $SbCl_5$, $SbF_5$, $BiF_5$, $OsF_5$, $ReF_5$, $MoF_5$, $WF_6$ and $WOF_4$; mixed halogen superacids such as $AlCl_{3-x}F_x$ where x can be 0-3; sulfonic superacids and anhydrides such as $FSO_2OH$, $F_3CSO_2OH$, $SO_3$, $F_3CSO_2OSO_2CF_3$, and acidic NAFION® resins; other protonic acids including the acid forms of fluorinated polyhedral boranes and carboranes such as the respective compositions $H_2B_{12}H_{12-x}F_x$ and $HCB_{11}H_{12-x}F_x$; superacids that are generated in situ by reaction with HF or another fluorinating agent to include $SbCl_5$, $BCl_3$, $PCl_5$, and $AlCl_3$; and mixtures of these and other superacids and acidic melts. NAFION® is a federally registered trademark of E. I. DU PONT DE NEMOURS AND COMPANY CORPORATION, Wilmington, Del. for resin compositions. The choice of superacid will depend upon the precursor compound I, the degree of fluorination desired, any safety considerations, and any requirements to avoid side reactions or improve yields. For example, the superacid can be non-oxidizing to the anion $[R_bZ_cB_dH_eF_y]$ and its products. The superacid may be present as a catalyst, as a stoichiometric reagent, or in an amount excess relative to the precursor I.

Examples of compounds which can be formed by the instant invention can comprise at least one member selected from the group consisting of a lithium fluorododecaborates of the formula:

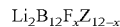

$$Li_2B_{12}F_xZ_{12-x}$$

where x is greater than or equal to 4 or 5 (average basis), typically at least 8, and in some cases at least 10 but less than or equal to 12, and Z represents H, Cl, and Br. Specific examples of lithium based fluorinated dodecaborates can comprise at least one member from the group consisting of: $Li_2B_{12}F_5H_7$, $Li_2B_{12}F_6H_6$, $Li_2B_{12}F_7H_5$, $Li_2B_{12}F_8H_4$, $Li_2B_{12}F_9H_3$, $Li_2B_{12}F_{10}H_2$, $Li_2B_{12}F_{11}H$, $Li_2B_{12}F_{12}$ and mixtures of salts with varying x such that the average x is equal to or greater than 5, or equal to 9 or 10, or $Li_2B_{12}F_xCl_{12-x}$ and $Li_2B_{12}F_xBr_{12-x}$ where x is 10 or 11.

The reactants may be combined in any order and at any rate to affect the desired fluorination chemistry, however, in some cases it may be useful to provide one or both of precursor compound I and SA diluted in HF or another solvent to affect safety and or process control factors as can be developed though good practices in chemistry and engineering.

The materials of construction for the reactor, as apparent to those skilled in the art, will have a role in the effectiveness of this invention as it pertains to the use of classically defined superacids. A reactor fabricated with components selected from copper, gold, aluminum, nickel, silver, platinum, palladium, carbon, TEFLON® resins, polyvinylchloride resins, polychlorotrifluoroethylene (e.g., KEL-F®) resins, hydrocarbon thermoplastics, sapphire, boron carbide, tantalum nitride, steel alloys, MONEL® alloys, HASTELLOY® alloys, and other similar materials would be suitable to observe the general advantages outlined in this invention. HASTELLOY® is a federally registered trademark of HAYNES INTERNATIONAL, INC., Kokomo, Ind. for alloy compositions. MONEL® is a federally registered trademark of HUNTINGTON ALLOYS CORPORATION, Huntington, WV. In some cases, the contact surfaces of the reactor can be composed of a form of TEFLON®, KEL-F®, sapphire, tantalum nitride, MONEL® alloy 400, MONEL® alloy 200, or HASTELLOY® C alloy 276 in order to enable the higher degrees of fluorination and preserve the reactor components from etching especially at higher temperatures and when stronger superacids are employed. KEL-F® is a federally registered trademark of MINNESOTA MINING AND MANUFACTURING COMPANY CORPORATION, St. Paul, Minn. for polychlorotrifluoroethylene resins. TEFLON® is a federally registered trademark of E. I. DU PONT DE NEMOURS AND COMPANY CORPORATION, Wilmington, Del. for polytetrafluoroethylene products.

The following examples are provided to illustrate certain aspects of the invention and do not limit the scope of the claims appended hereto. Mass balance, mass spectrometry and NMR were used in accordance with conventional methods to detect the reaction products referenced below.

EXAMPLES

A reaction mixture for fluorination of boron hydrides was prepared. $BF_3$ and HF were supplied by Air Products & Chemicals, Inc. (Allentown, Pa.). $TaF_5$ and $SbF_5$ were obtained from Sigma-Aldrich (Milwaukee, Wis.) and were treated with a mixture of $F_2$ and $N_2$ gases (AiroPak, Air Products & Chemicals) to remove moisture and/or oxygenated materials. Potassium dodecahydrododecaborate methanolate ($K_2B_{12}H_{12}$—MeOH, Callery Chemical Co., Pittsburgh, Pa.) was treated to remove methanol. Tetraethylammonium bromide was obtained from Sigma-Aldrich. Water in the examples is deionized water unless otherwise indicated. Reactors were cleaned to remove contaminants then were vacuum-dried and $F_2$ passivated prior to use. HF and $BF_3$ were transferred into a reactor vessel at $-78°$ C. The charged reactors were allowed to warm to ambient temperature (e.g., 20-25° C.) then heated to the desired temperature for the desired amount of time. Following each reaction the reactor contents were cooled to room temperature, volatile components were evacuated and the crude product was rinsed from the reactor with water. The rinsate was neutralized to pH 12-13 and filtered. In all cases a clear, colorless solution was obtained as a filtrate to which an excess of aqueous tetraethylammonium ("TEA") bromide was added to precipitate the product as a fine powder that was captured by filtration. The filter cake was rinsed with warm water to remove impurities until the pH of the filtrate became substantially neutral. The solid product was then vacuum dried.

Comparative Example 1

Reaction of $K_2B_{12}H_{12}$ with HF at 20° C. in Stainless Steel 1.00 g of $K_2B_{12}H_{12}$ (220.02 g/mol, 4.5 mmol) was charged to a 100 mL SS Parr reactor followed by 20 g of HF at $-78°$ C. The reactor was warmed to 20° C. and was allowed to stir for 16 hours. Following the removal of HF under vacuum the product was purified and analyzed as outlined above providing 1.89 g (ca. 91% yield) of (tetraethylammonium (TEA))$_2$ $B_{12}H_9F_3$ ($MW_{ave}$=456.30 g/mol). Percentages are on a weight basis, unless specifically indicated otherwise.

Comparative Example 2

Reaction of $K_2B_{12}H_{12}$ with HF at 20° C. in a Teflon-Lined Vessel

Comparative Example 1 was repeated except using a Hastalloy C-276 Parr reactor with TEFLON® liner in place of the stainless steel reactor. The isolated product consisted of 1.91 g (ca. 92% yield) of product $(TEA)_2B_{12}H_{12-x}F_x$ with 93 mol % (i.e., percentage on a molar basis) where x=3 and 7 mol % where x=4 ($MW_{ave}$=474.29 g/mol).

Example 1

Reaction of $K_2B_{12}H_{12}$ with HF and BF3 at 20° C. in Stainless Steel 1.00 g of $K_2B_{21}H_{12}$ (220.02 g/mol, 4.5 mmol) was charged to a 100 mL SS Parr reactor followed by 20 g of HF at $-78°$ C. The reactor was warmed to 20° C. and was allowed to stir for 16 hours. $BF_3$ (ca. 18 mmol, 4 equivalents relative to $K_2B_{12}H_{12}$) was added to the reactor following HF addition. The product was then isolated and found to have 1.95 g (ca. 90% yield) of product $(TEA)_2B_{12}H_{12-x}F_x$ with 84 mol % where x=4 and 16 mol % where x=5 ($MW_{ave}$=492.28 g/mol).

Example 2

Reaction of $K_2B_{12}H_{12}$ with HF and Excess $BF_3$ at 20° C. in Stainless Steel Example 1 was repeated except 45 mmol $BF_3$ (ca., 10 equivalents relative to $K_2B_{12}H_{12}$) was added to the reactor following HF addition rather than 18 mmol $BF_3$. The isolated product consisted of 1.95 g (ca. 88% yield) of product $(TEA)_2B_{12}H_{12-x}F_x$ with 29 mol % where x=4, 70 mol % where x=5, and approximately 1 mol % where x=6 ($MW_{ave}$=510.27 g/mol).

Example 3

Reaction of $K_2B_{12}H_{12}$ with HF and $BF_3$ at 60° C. in Stainless Steel

Example 1 was repeated except at 60° C. as a reaction temperature rather than 20° C. The isolated product consisted of 2.09 g (ca. 90% yield) of product $(TEA)_2B_{12}H_{12-x}F_x$ with 3 mol % where x=5, 95 mol % where x=6, and 2 mol % where x=7 ($MW_{ave}$=528.26 g/mol).

Example 4

Reaction of $K_2B_{12}H_{12}$ with HF and $BF_3$ at 120° C. in Stainless Steel

Example 1 was repeated except at 120° C. as a reaction temperature rather than 20° C. The crude material isolated from the reactor possessed considerable color indicating leaching of iron and/or chromium. The isolated product consisted of 1.94 g (ca. 81% yield) of product $(TEA)_2B_{12}H_{12-x}F_x$ with 3 mol % where x=6, 94 mol % where x=7, and 3 mol % where x=8 ($MW_{ave}$=546.25 g/mol).

Example 5

Reaction of $K_2B_{12}H_{12}$ with HF and Excess $BF_3$ at 120° C. in Stainless Steel Example 2 was repeated except at 120° C. as a reaction temperature rather than 20° C. The crude material isolated from the reactor possessed considerable color indicating leaching of iron and/or chromium. The isolated product consisted of 1.84 g (ca. 77% yield) of product $(TEA)_2B_{12}H_{12-x}F_x$ with 8 mol % where x=6, 91 mol % where x=7, and approximately 1 mol % where x=8 ($Mw_{ave}$=546.25 g/mol).

Example 6

Reaction of $K_2B_{12}H_{12}$ with HF and $BF_3$ at 120° C. in a TEFLON®-Lined Vessel Example 5 was repeated except using a Hastalloy C-276 Parr reactor with TEFLON® liner in place of the stainless steel reactor. The isolated product consisted of 2.18 g (ca. 89% yield) of product $(TEA)_2B_{12}H_{12-x}F_x$ with 38 mol % where x=7, 62 mol % where x=8.

Example 7

Reaction of $K_2B_{12}H_{12}$ with HF and Catalytic $BF_3$ at 120° C. in a TEFLON®-Lined Vessel Example 6 was repeated except 2.5 mmol $BF_3$ (ca., 0.6 equivalents relative to $K_2B_{12}H_{12}$) were added to the reactor following HF addition rather than 18 mmol $BF_3$. The isolated product consisted of 2.19 g (ca. 90% yield) of product $(TEA)_2B_{12}H_{12-x}F_x$ with 58 mol % where x=7, and approximately 42 mol % where x=8.

Example 8

Scaled Reaction of $K_2B_{12}H_{12}$ with HF and Catalytic $BF_3$ at 120° C. in a TEFLON®-Lined Vessel 5.00 g of $K_2B_{12}H_{12}$ (23 mmol) were charged to a 300 mL Hastalloy C-276 Parr reactor with TEFLON® liner followed by 100 g of HF and $BF_3$ (ca. 13.8 mmol, 0.6 equivalents relative to $K_2B_{12}H_{12}$) at −78° C. The reactor was warmed to 20° C. then was heated to 120° C. and held at 120° C. for 16 hours. Following the removal of HF under vacuum the product was purified and analyzed as outlined above providing 10.52 g (ca. 86% yield) of product $(TEA)_2B_{12}H_{12-x}F_x$ with 45 mol % where x=7 and 55 mol % where x=8.

Example 9

Reaction of $K_2B_{12}H_{12}$ with HF and $TaF_5$ at 20° C. in a fluorinated ethylene propylene (FEP) Tube A Teflon tee was fitted with a valve and 2 FEP reaction tubes. 0.20 g of $K_2B_{12}H_{12}$ (0.9 mmol) were charged to one FEP tube and 1.00 g of $TaF_5$ (275.94 g/mol, 3.6 mmol, 4 equivalents relative to $K_2B_{12}H_{12}$) were loaded to the other FEP tube. 4 g of HF were added to the tube containing $K_2B_{12}H_{12}$ at −78° C. and the $TaF_5$ was allowed to deliquesce with HF vapor at room temperature. The reactor was allowed to warm to 20° C during which $H_2$ gas evolution was observed. After 2 hours the gas evolution had ceased and the $TaF_5$—HF solution was slowly poured into the tube containing the borate salt giving rise to immediate and vigorous evolution of additional $H_2$. The reactor contents were allowed to stand for 16 hours maintaining a clear and colorless solution throughout indicating that $TaF_5$ was not reduced. Following the removal of HF under vacuum the product was purified and analyzed as outlined above providing 0.43 g (ca. 86% yield) of product $(TEA)_2B_{12}H_{12-x}F_x$ with 10 mol % where x=5 and 90 mol % where x=6.

Comparative Example 3

Reaction of $K_2B_{12}H_{12}$ with HF and $TaF_5$ at 60° C. in Stainless Steel 1.00 g of $K_2B_{12}H_{12}$ (4.5 mmol) and 4.92 g of $TaF_5$ (18 mmol, 4 equivalents relative to $K_2B_{12}H_{12}$) were carefully charged to a 100 mL stainless steel Parr reactor followed by 20 g of HF at −78° C. The reactor was warmed to 20° C. then was heated to 60° C. with stirring for 16 hours. Following the removal of HF under vacuum the product was purified and analyzed as outlined above providing 1.58 g (ca. 69% yield) of product $(TEA)_2B_{12}H_{12-x}F_x$ with 45 mol % where x=5, 54 mol % where x=6, and approximately 1 mol % where x=7. The crude product possessed a deep green color indicating the presence of iron and/or chromium and the surfaces of the reactor were observed to be pitted.

Comparative Example 4

Reaction of $K_2B_{12}H_{12}$ with HF and $TaF_5$ at 120° C. in Stainless Steel

Comparative Example 3 was repeated except at 120° C. as a reaction temperature rather than 60° C. The isolated product consisted of 1.21 g (ca. 52% yield) of product $(TEA)_2B_{12}H_{12-x}F_x$ with 89 mol % where x=6, 11 mol % where x=7. The crude product possessed a deep color appearing black and pitting to the reactor surfaces damaged the reactor beyond repair.

Example 10

Reaction of $K_2B_{12}H_{12}$ with HF and $TaF_5$ at 120° C. in a Teflon-Lined Vessel The steps of Comparative Example 4 were repeated except using a Hastalloy C-276 Parr reactor with teflon liner in place of the stainless steel reactor. The isolated product consisted of 2.17 g (ca. 87% yield) of product $(TEA)_2B_{12}H_{12-x}F_x$ with 80 mol % where x=8 and 20 mol % where x=9 ($MW_{ave}$=564.24 g/mol). The crude product contained a small amount of a black solid indicating the potential reduction of a tiny quantity of $TaF_5$.

Comparative Example 5

Reaction of $K_2B_{12}H_{12}$ with HF and $SbF_5$ at 20° C. in an FEP Tube

A Teflon tee was fitted with a valve and 2 FEP reaction tubes. 0.20 g of $K_2B_{12}H_{12}$ (0.9 mmol) were charged to a one FEP tube followed by 4 g of HF at −78° C. The reactor contents were allowed to warm to 20° C. and evolve $H_2$ for 2 hours. After removing the HF, 0.90 g of $SbF_5$ (216.75 g/mol, 4.2 mmol, 4.5 equivalents relative to $K_2B_{12}H_{12}$) were loaded to the empty FEP tube. 4 g of HF were added to the tube containing the borate salt at −78° C. and the $SbF_5$ absorbed HF vapor at room temperature. The reactor were warmed to 20° C. and the $SbF_5$–HF solution was slowly poured into the tube containing the borate salt solution producing immediate precipitation of colorless solids throughout the addition but no $H_2$ gas evolution. The reactor contents were allowed to stand for 16 hours. Following the removal of HF under vacuum the product was purified and analyzed as outlined above providing 0.40 g (ca. 80% yield) of product $(TEA)_2B_{12}H_{12-x}F_x$ with 8 mol % where x=7, 32 mol % where x=8, 55 mol % where x=9, and 5 mol % where x=10 ($MW_{ave}$=582.23 g/mol). The cascading distribution of fluorinated products and reaction precipitate in this example indicate that $SbF_5$ may be primarily acting as an oxidative fluorinating agent rather than a superacid.

While the invention has been described with reference to a certain aspects or embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A process for fluorination of borohydride salts comprising:
   providing a reaction medium comprising HF and at least one superacid additive;
   providing a borohydride salt compound to the reaction medium having the following formula:

$$M_a[R_bZ_cB_dH_eF_y]_k$$

wherein M is a cation having a valence from 1 to 4; R is selected from the group consisting of a halogen group, hydroxyl group, amino group, nitro group, alkyl group, alkoxy group, perfluoroalkoxy group, phenyl group and combinations thereof; Z is selected from the group consisting of C, Si, Ge, Sn, Pb, N, P, As, Sb, Bi and combinations thereof; B is boron; H is hydrogen; F is fluorine; a is 1 or 2; b is an integer from 0 to 11, c is an integer from 0 to 1; d is an integer from 5 to 12; e is an integer from 1 to 12; and y is an integer from 0 to 11; k is 1, 2, or 3; and
   reacting the borohydride salt with the reaction medium under conditions for formation of a fluorinated borohydride salt having the formula:

$$M_a[R_bZ_cB_dH_{e-n}F_{y+n}]_k$$

wherein n is an integer from 1 to e and y+n is greater than or equal to 5.

2. The process of claim 1, wherein the M cation comprises at least one member selected from the group consisting of a hydrogen, alkali metal, and alkaline earth metal.

3. The process of claim 1, wherein the M cation comprises at least one member selected from the group consisting of hydrogen, hydronium ($H_3O^+$), ammonium, tetraalkylammonium, trialkylammonium, alkali metals, alkaline earth metals, tetraalkylphosphonium, and transition metals such as zinc, silver, iron, nickel, tantalum, and cerium.

4. The process of claim 1, wherein b and c are 0.

5. The process of claim 1, wherein d is an integer selected from the group consisting of 10 and 12.

6. The process of claim 1, wherein the superacid additive comprises at least one member selected from the group consisting of $AlCl_3$, $AlF_3$, $BCl_3$, $BF_3$, $GaF_3$, $VF_5$, $NbF_5$, $TaF_5$, $PCl_5$, $PF_5$, $AsF_5$, $SbCl_5$, $SbF_5$, $BiF_5$, $OsF_5$, $ReF_5$, $MoF_5$, $WF_6$, $WOF_4$, mixed halogen superacids, sulfonic superacids and anhydrides, protonic acids, superacid reaction products of HF or another fluorinating agent and $SbCl_5$, $BCl_3$, $PCl_5$, or $AlCl_3$ and combinations thereof.

7. The process of claim 1, wherein the reaction medium further includes a transfer medium.

8. The process of claim 1, wherein the transfer medium comprises at least one member selected from the group consisting of $SO_2ClF$, $SO_2$, perfluorinated liquids, chlorofluorocarbons, and hydrofluorocarbons.

9. The process of claim 1, wherein the reacting step takes place at a temperature of less than about 120° C.

10. A process for fluorination of borohydride salts comprising:
    fluorinating a borohydride salt compound having the following formula:

$$M_a[R_bZ_cB_dH_eF_y]_k$$

in the presence of at least one superacid additive and HF in a reactor vessel fabricated from a material resistant to superacid compositions to form a compound having the following formula:

$$M_a[R_bZ_cB_dH_{e-n}F_{y+n}]_k$$

wherein M is a cation having a valence from 1 to 4; R is selected from the group consisting of a halogen group, hydroxyl group, amino group, nitro group, alkyl group, alkoxy group, perfluoroalkoxy group, phenyl group and combinations thereof; Z is selected from the group consisting of C, Si, Ge, Sn, Pb, N, P, As, Sb, Bi and combinations thereof; B is boron; H is hydrogen; F is fluorine; a is 1 or 2; b is an integer from 0 to 11, c is an integer from 0 to 1; d is an integer from 5 to 12; e is an integer from 1 to 12; and y is an integer from 0 to 11; k is 1, 2, or 3; and n is an integer from 1 to e and y+n is greater than or equal to 5.

11. The process of claim 10, wherein the reactor vessel is fabricated from at least one material selected from the group consisting of copper, gold, aluminum, nickel, silver, platinum, palladium, carbon, polytetrafluoroethylene resins, polyvinylchloride resins, polychlorotrifluoroethylene resins, hydrocarbon thermoplastics, sapphire, boron carbide, tantalum nitride, steel alloys, superalloys, and combinations thereof.

12. The process of claim 10 wherein the M cation comprises at least one member selected from the group consisting of a hydrogen, alkali metal, and alkaline earth metal.

13. The process of claim 10, wherein the M cation comprises at least one member selected from the group consisting of hydrogen, hydronium ($H_3O^+$), ammonium, tetraalkylammonium, trialkylammonium, alkali metals, alkaline earth metals, tetraalkylphosphonium, and transition metals such as zinc, silver, iron, nickel, tantalum, and cerium.

14. The process of claim 10, wherein b and c are 0.

15. The process of claim 10, wherein d is an integer selected from the group consisting of 10 and 12.

16. The process of claim 10, wherein the superacid additive comprises at least one member selected from the group consisting of $AlCl_3$, $AlF_3$, $BCl_3$, $BF_3$, $GaF_3$, $VF_5$, $NbF_5$, $TaF_5$, $PCl_5$, $PF_5$, $AsF_5$, $SbCl_5$, $SbF_5$, $BiF_5$, $OsF_5$, $ReF_5$, $MoF_5$, $WF_6$, $WOF_4$, mixed halogen superacids, sulfonic superacids and anhydrides, protonic acids, superacid reaction products of HF or another fluorinating agent and $SbCl_5$, $BCl_3$, $PCl_5$, or $AlCl_3$, and combinations thereof.

17. The process of claim 10, wherein the reacting step takes place at a temperature of less than about 120° C.

18. The process of claim 10 wherein the compound comprises $Li_2B_{12}F_xZ_{12-x}$ where x is less than or equal to 12, and Z represents H, Cl, and Br.

* * * * *